United States Patent
Xiao et al.

(10) Patent No.: US 12,144,556 B2
(45) Date of Patent: Nov. 19, 2024

(54) SYSTEMS AND METHODS FOR SURGICAL TRAJECTORY PLANNING

(71) Applicant: Valorbec, Société en commandite, Quebec (CA)

(72) Inventors: Yiming Xiao, Verdun (CA); Owen Hellum, Montreal (CA)

(73) Assignee: Valorbec, Société en commandite, Quebec (CA)

( * ) Notice: Subject to any disclaimer, the term of this patent is extended or adjusted under 35 U.S.C. 154(b) by 109 days.

(21) Appl. No.: 17/952,847

(22) Filed: Sep. 26, 2022

(65) Prior Publication Data

US 2024/0000509 A1     Jan. 4, 2024

Related U.S. Application Data

(60) Provisional application No. 63/357,102, filed on Jun. 30, 2022.

(51) Int. Cl.
*G06T 17/00* (2006.01)
*A61B 34/10* (2016.01)
(Continued)

(52) U.S. Cl.
CPC .............. *A61B 34/10* (2016.02); *A61B 90/39* (2016.02); *G06F 3/013* (2013.01); *G06T 17/00* (2013.01);
(Continued)

(58) Field of Classification Search
CPC ... A61B 34/10; A61B 90/39; A61B 2034/105; A61B 2034/107; A61B 2090/061;
(Continued)

(56) References Cited

U.S. PATENT DOCUMENTS 9,594,877 B2   3/2017  Kaula et al.
2012/0056986 A1*  3/2012  Popovic .................. A61B 1/04
                                                       348/45

(Continued)

FOREIGN PATENT DOCUMENTS

CN    111249622 A    6/2020
KR    20200068239 A  6/2020

OTHER PUBLICATIONS

Holden, M., Zhao, Y., Haegelen, C., Essert, C., Vidal S, Bardinet E, Ungi T, Fichtinger G, Jannin P. 2018. Self-guided training for deep brain stimulation planning using objective assessment. Int J Comput Assist Radiol Surg. 13(7):1129-1139.

(Continued)

*Primary Examiner* — Jitesh Patel (57) ABSTRACT

A method for surgical trajectory planning, particularly useful for deep brain stimulation. A three-dimensional model of an anatomical structure is rendered, which includes a target site. As the user gazes into the model, eye tracking data is obtained and a line of sight for the target site is identified. A surgical trajectory is determined along the line of sight between the target site and a surgical entry point on the surface of the anatomical structure. The method allows the identification of an optimal surgical trajectory to reach the target site while avoiding key structures within the anatomical structure, such as blood vessels, sulci, ventricles. Advantageously, the model is rendered in a virtual environment, and the eye tracking data is obtained from a VR headset.

26 Claims, 5 Drawing Sheets

(51) Int. Cl.
*A61B 90/00* (2016.01)
*G06F 3/01* (2006.01)

(52) U.S. Cl.
CPC ... *A61B 2034/105* (2016.02); *A61B 2034/107* (2016.02); *A61B 2090/061* (2016.02); *A61B 2090/062* (2016.02); *A61B 2090/365* (2016.02); *A61B 2090/3983* (2016.02)

(58) Field of Classification Search
CPC ........ A61B 2090/062; A61B 2090/365; A61B 2090/3983; A61B 34/20; A61B 2034/2055; G06F 3/013; G06T 17/00
See application file for complete search history.

(56) References Cited

U.S. PATENT DOCUMENTS

| | | | |
|---|---|---|---|
| 2020/0335221 A1 | 10/2020 | Fichtinger et al. | |
| 2022/0007991 A1* | 1/2022 | Roberts | G06T 7/33 |
| 2022/0096158 A1* | 3/2022 | Flossmann | G06T 7/70 |
| 2022/0110682 A1* | 4/2022 | Tseng | G06T 19/20 |
| 2022/0287676 A1* | 9/2022 | Steines | G02B 27/0172 |
| 2022/0409301 A1* | 12/2022 | Liu | A61B 34/32 |

OTHER PUBLICATIONS

Beriault S, Drouin S, Sadikot AF, Xiao Y, Collins DL, Pike GB. 2013. A Prospective Evaluation of Computer-Assisted Deep Brain Stimulation Trajectory Planning. Clinical Image-Based Procedure. From Planning to Intervention: International Workshop, CLIP 2012, Held in Conjunction with MICCAI 2012, 7761: 42-49.

Alaraj A, Luciano CJ, Bailey DP, Elsenousi A, Roitberg BZ, Bernardo A, Banerjee PP, Charbel FT. 2015. Virtual reality cerebral aneurysm clipping simulation with real-time haptic feedback. Neurosurgery. 11 Suppl 2:52-58.

Stadie AT, Kockro RA, Reisch R, Tropine A, Boor S, Stoeter P, Perneczky A. Virtual reality system for planning minimally invasive neurosurgery. Technical note. J Neurosurg. 2008;108(2):382-94.

Petersen MV, Mlakar J, Haber SN, Parent M, Smith Y, Strick PL, Griswold MA, McIntyre CC. Holographic Reconstruction of Axonal Pathways in the Human Brain. Neuron. 2019;104(6):1056-1064.e3.

Deora H, Pruthi N, Rao KVLN, Saini J, Dikshit P. Predicting the Ideal Ventricular Freehand Pass Trajectory Using Osirix Software and the Role of Occipital Shape Variations. World Neurosurg. Sep. 2020;141:e341-e357. doi: 10.1016/j.wneu.2020.05.146. Epub May 23, 2020. PMID: 32454198.

Hasegawa H, Shin M, Kin T, Saito N. Fully Endoscopic Minimally Invasive Tumor Resection for Cystic Cerebellar Hemangioblastoma. World Neurosurg. Jun. 2019;126:484-490. doi: 10.1016/j.wneu.2019.03.158. Epub Mar. 26, 2019. PMID: 30922906.

Sun GC, Chen XL, Hou YZ, Yu XG, Ma XD, Liu G, Liu L, Zhang JS, Tang H, Zhu RY, Zhou DB, Xu BN. Image-guided endoscopic surgery for spontaneous supratentorial intracerebral hematoma. J Neurosurg. Sep. 2017;127(3):537-542. doi: 10.3171/2016.7.JNS16932. Epub Sep. 16, 2016. PMID: 27636179.

Qiu TM, Zhang Y, Wu JS, Tang WJ, Zhao Y, Pan ZG, Mao Y, Zhou LF. Virtual reality presurgical planning for cerebral gliomas adjacent to motor pathways in an integrated 3-D stereoscopic visualization of structural MRI and DTI tractography. Acta Neurochir (Wien). Nov. 2010;152(11):1847-57. doi: 10.1007/s00701-010-0739-x. Epub Jul. 22, 2010. PMID: 20652607.

R. R. Shamir et al., "Trajectory planning with Augmented Reality for improved risk assessment in image-guided keyhole neurosurgery," 2011 IEEE International Symposium on Biomedical Imaging: From Nano to Macro, 2011, pp. 1873-1876, doi: 10.1109/ISBI.2011.5872773.

\* cited by examiner

SYSTEMS AND METHODS FOR SURGICAL TRAJECTORY PLANNING

FIELD

The various embodiments described herein generally relate to one or more systems and methods for planning surgical trajectories.

BACKGROUND

Surgeons usually carefully plan surgical procedures prior to entering the operating room. One crucial step in planning surgical procedures is trajectory planning, that is, planning the path between the entry point on the surface of the patient's body and the surgical site.

Careful trajectory planning can reduce the risk of encountering crucial structures during a surgical procedure, which can reduce operating time, thereby reducing risks of infection, and reduce the risk of complications. Currently, most methods of surgical trajectory planning require surgeons to review multiple two-dimensional and occasionally, three-dimensional images of the anatomical structure requiring surgery, create a mental model of the anatomical structure, and devise a surgical trajectory using the mental model. This method is time-consuming, even for experienced surgeons, susceptible to error, and imposes a significant cognitive burden on the surgeon. If the mental model is incorrect, the surgeon is often required to adjust the surgical path in the operating room, which can increase operating time.

SUMMARY OF VARIOUS OF EMBODIMENTS

Various embodiments of a system and method for surgical trajectory planning are provided according to the teachings herein.

In one aspect, there is provided a method for surgical trajectory planning, the method comprising:
- rendering a three-dimensional model of an anatomical structure, said model including a target site within said anatomical structure;
- obtaining eye tracking data of a user as said user is gazing into said model and towards said target site;
- identifying a line of sight for the target site based on a point of gaze of a user;
- determining a surgical trajectory along said line of sight between the target site and a surgical entry point on a surface of the anatomical structure, the surgical entry point corresponding to an intersection of the surgical trajectory and said surface of the three-dimensional model.

In another aspect, there is provided a system for surgical trajectory planning in a three-dimensional model of an anatomical structure, said model including a target site within said anatomical structure, the system comprising:
- an electronic device comprising at least one processor configured to:
  - obtain eye tracking data of a user as said user gazes into said model towards said target site;
  - identify a line of sight for the target site based on a point of gaze of said user;
  - determine a surgical trajectory along said line of sight between the target site and a surgical entry point on a surface of the anatomical structure, the surgical entry point corresponding to an intersection of the surgical trajectory and said surface of the three-dimensional model;
  - wherein said surgical trajectory traces a path to said target site while avoiding key structures.

It will be appreciated that the foregoing summary sets out representative aspects of embodiments to assist skilled readers in understanding the following detailed description. Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Further aspects and features of the example embodiments described herein will appear from the following description taken together with the accompanying drawings.

DETAILED DESCRIPTION OF THE EMBODIMENTS

The headings and Abstract of the Disclosure provided herein are for convenience only and do not interpret the scope or meaning of the embodiments.

Various embodiments in accordance with the teachings herein will be described below to provide examples of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context.

Unless the context requires otherwise, throughout the specification and claims which follow, the word "comprise" and variations thereof, such as, "comprises" and "comprising" are to be construed in an open, inclusive sense, that is, as "including, but not limited to".

Various terms used throughout the present description may be read and understood as follows, unless the context indicates otherwise: singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

Reference throughout this specification to "one embodiment", "an embodiment", "at least one embodiment" or "some embodiments" means that one or more particular features, structures, or characteristics may be combined in any suitable manner in one or more embodiments, unless otherwise specified to be not combinable or to be alternative options.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

Similarly, throughout this specification and the appended claims the term "communicative" as in "communicative pathway," "communicative coupling," and in variants such as "communicatively coupled," is generally used to refer to any engineered arrangement for transferring and/or exchanging information. Examples of communicative pathways include, but are not limited to, electrically conductive pathways (e.g., electrically conductive wires, physiological signal conduction), electromagnetically radiative pathways (e.g., radio waves), or any combination thereof. Examples of communicative couplings include, but are not limited to, electrical couplings, magnetic couplings, radio couplings, or any combination thereof.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," to, at least, provide," "to, at least, transmit," and so on.

A portion of the example embodiments of the systems, devices, or methods described in accordance with the teachings herein may be implemented as a combination of hardware or software. For example, a portion of the embodiments described herein may be implemented, at least in part, by using one or more computer programs, executing on one or more programmable devices comprising at least one processing element, and at least one data storage element (including volatile and non-volatile memory). These devices may also have at least one input device (e.g., a keyboard, a mouse, a touchscreen, and the like) and at least one output device (e.g., a display screen, a printer, a wireless radio, and the like) depending on the nature of the device.

It should also be noted that there may be some elements that are used to implement at least part of the embodiments described herein that may be implemented via software that is written in a high-level procedural language such as object-oriented programming. The program code may be written in C, C++ or any other suitable programming language and may comprise modules or classes, as is known to those skilled in object-oriented programming. Alternatively, or in addition thereto, some of these elements implemented via software may be written in assembly language, machine language, or firmware as needed.

At least some of the software programs used to implement at least one of the embodiments described herein may be stored on a storage media or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The program code may be preinstalled and embedded during manufacture and/or may be later installed as an update for an already deployed computing system. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

Accordingly, any module, unit, component, server, computer, terminal or device described herein that executes software instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by an application, module, or both. Any such computer storage media may be part of the device or accessible or connectable thereto.

Described herein are various example embodiments of methods and systems that may be used for planning surgical trajectories using eye tracking data obtained from an eye tracking device. The various example embodiments described herein can display three-dimensional models of anatomical structures, receive selections of target sites that can correspond to surgical sites and determine surgical trajectories between surgical entry points and target sites. The surgical planning trajectory system may be used by surgeons to visualize and plan surgical trajectories prior to performing surgeries and reduce the likelihood of crucial structures such as blood vessels being impacted during surgery. The various embodiments described herein may additionally decrease the time required for surgical trajectory planning, which can increase efficiency.

Conventional methods for surgical trajectory planning typically require surgeons to rely on and analyze two-dimensional images or resliced tree-dimensional images of a patient's anatomy and plan a surgical route by devising a mental model of the patient's anatomy in three dimensions. This process is time consuming even for experienced surgeons and is susceptible to human error. When operating on a complex anatomical structure, such as the brain, this process can pose considerable challenges to a surgeon's cognitive load and spatial memory skills. The optimal surgical trajectory path is one that reaches the target site while avoiding key structures within the anatomy of the patient. Key structures, as will be seen hereinafter, include blood vessels, sulci, and in the case of the brain, ventricles. Other key structures may be relevant depending on the specific area of interest. Some trajectory planning methods involve optimizing cost functions; however, these strategies required the weights to be defined by a user through trial-and-error. Inadequate surgical trajectories can require additional trial-and-error adjustments during surgery, resulting in prolonged surgical time and thereby increased risks of infections, and potential hemorrhages and other adverse side effects.

At least some of the embodiments described herein may be implemented in a virtual reality environment. Such embodiments can involve, for example, a head-mounted virtual reality device. At least some of these embodiments can involve the eye tracking device being housed within the head-mounted virtual reality device.

At least some of the embodiments described herein may be used for planning surgical trajectories for placing deep brain stimulation (DBS) electrodes in a subject's brain. Deep brain stimulation can be used for treating movement disorders in patients, including Parkinson's disease, essential tremor, dystonia, obsessive-compulsive disorder and epilepsy. DBS is a minimally invasive procedure that only requires the creation of a small bur-hole in the skull and is particularly suited for surgical trajectory planning as it involves minimal intra-operative tissue shift, reducing the need for tissue shift to be modelled in the three-dimensional model.

In at least one example embodiment described herein, the surgical trajectory planning system may employ a Voodoo doll interaction method. In the context of the present invention, the voodoo doll interaction method advantageously uses two sets of digital 3D models. One model, for example model A, contains all of the structure of the anatomical structure. Another model, for example model B, only contains a sub-set of the full model. In some cases, model B contains only one structure, i.e. the STN. Actions on model B, such as annotations, spatial manipulations, are transferred to model A to allow better precision and ease. In this sense, model B behaves as a "voodoo doll".

In at least one embodiment, the quality of the surgical trajectory determined may be assessed and displayed using for example, various metrics. For example, the quality of the surgical trajectory may be determined based on an assessment of the level of risk associated with the surgical trajectory.

In at least one embodiment, the level of risk may vary based on the distance between the surgical trajectory and key structures in the anatomical structure.

In at least one embodiment, the metrics may be displayed along the three-dimensional model of the anatomical structure.

Figure 1:
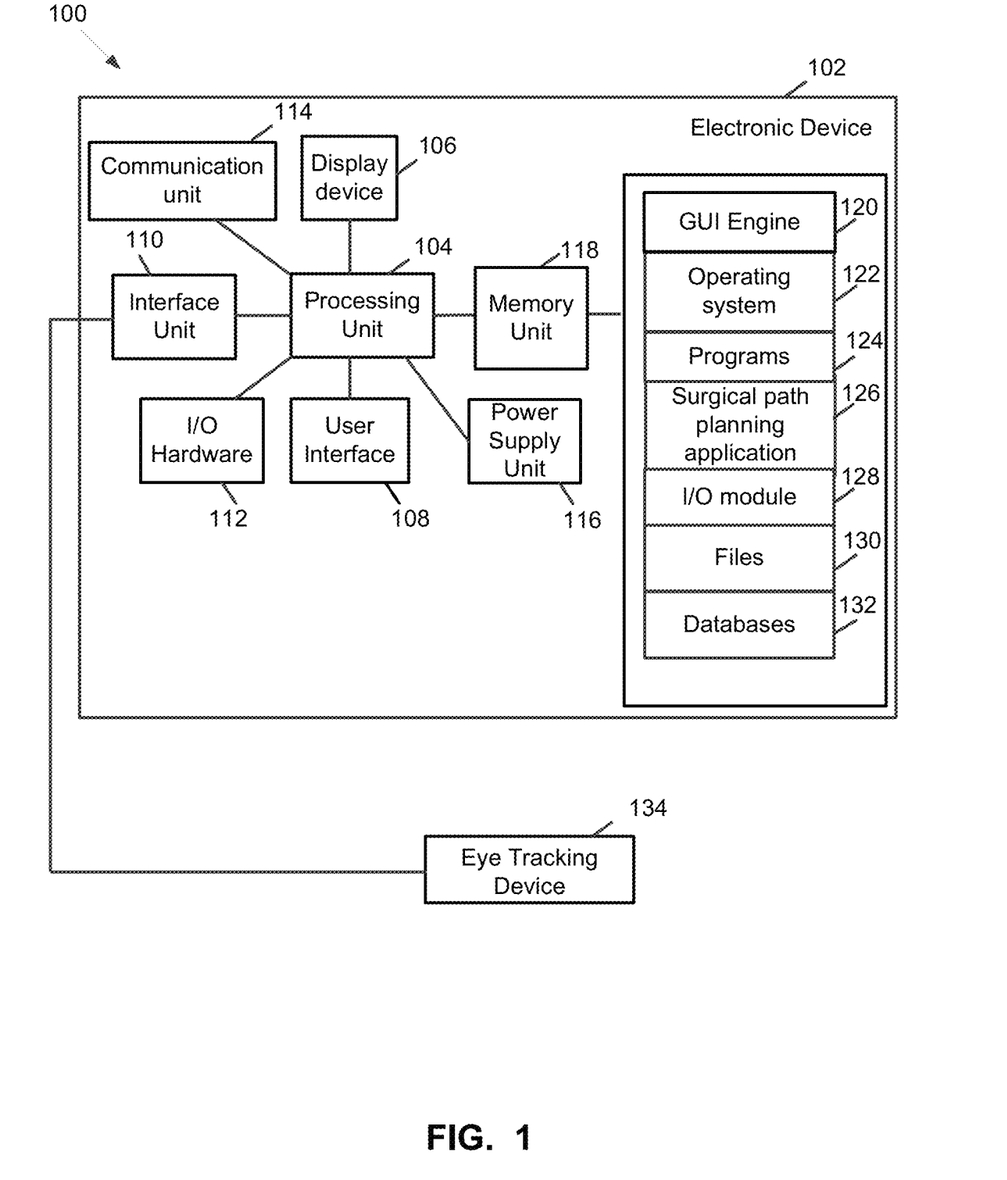
FIG. 1 shows a block diagram of an example embodiment of a system for surgical trajectory planning.

Referring now to FIG. 1, shown therein is a block diagram of an example embodiment of a system 100 that can be used for surgical trajectory planning.

The system 100 includes an electronic device 102 and an eye tracking device 134. The system 100 is provided as an example and there can be other embodiments of the system 100 with different components or a different configuration of the components described herein. The system 100 further includes one or more power supplies (not shown) connected to various components of the system 100 for providing power thereto as is commonly known to those skilled in the art. In general, a user may interact with the electronic device 102 to view a three-dimensional model of the anatomical structure requiring surgery of the patient, identify and select a target site for the surgery, determine the optimal viewing angle, view the surgical entry point, view the surgical trajectory and review metrics associated with the surgical trajectory. The electronic device 102 can interact with the eye tracking device 134 to obtain eye tracking data and determine a point of gaze of the user.

The electronic device 102 includes a processing unit 104, a display device 106, a user interface 108, an interface unit 110, input/output (I/O) hardware 112, a communication unit 114, a power supply unit 116, and a memory unit 118. The memory unit 118 includes random access memory ("RAM") and non-volatile storage for storing data files and software code for various programs such as those used to provide a Graphical User Interface (GUI) engine 120, an operating system 122 and other programs 124 as well as software modules such as a surgical trajectory planning application 126, an I/O module 128, files 130 and one or more databases 132 that collectively are used perform various functions related to surgical trajectory planning and/or displaying metrics related to a surgical trajectory. Various components of the electronic device 102 may be connected by a communication bus to facilitate communication therebetween and a power bus to receive power from the power supply unit 116.

The processing unit 104 controls the operation of the electronic device 102 and can be any suitable processor, controller or digital signal processor that can provide sufficient processing power processor depending on the configuration, purposes and requirements of the system 100 as is known by those skilled in the art. For example, the processing unit 104 may be a high-performance general processor. In alternative embodiments, the processing unit 104 may include more than one processor with each processor being configured to perform different dedicated tasks. In alternative embodiments, specialized hardware can be used to provide some of the functions provided by the processing unit 104.

The display device 106 can be any suitable display that provides visual information depending on the implementation of the electronic device 102. For instance, the display device 106 can be a VR head-mounted device display if the electronic device 102 is a VR head-mounted device or an apparatus that is adapted to render or provide the impression of rendering a three-dimensional object. Advantageously, the display device 106 can display three-dimensional models of anatomical structures, surgical trajectories and metrics associated with the surgical trajectories. It will be understood that although the present description is presently preferably adapted for use in a virtual reality or mixed reality environment, holograms or other three-dimensional renderings of an object are within the scope of the present claims.

The user interface 108 enables a user to provide input via one or more input devices, which may include, but is not limited to, a handheld controller, a mouse, a keyboard, a trackpad, a thumbwheel, a trackball, voice recognition, a touchscreen, one or more push buttons, and/or a scroll wheel, for example, depending on the implementation of the electronic device 102. The user interface 108 also outputs information to one or more output devices, which may include, for example, the display 106, a printer and/or a speaker. In some cases, the display 106 may be used to provide one or more GUIs through an Application Programming Interface. A user may then interact with the one or more GUIs via the user interface 108 for configuring the electronic device 102 to operate in a certain fashion and/or providing input data.

The interface unit 110 can be any interface that allows the electronic device 102 to send and receive signals with other devices external to the electronic device 102 such as sensors, signal processing hardware, other electronic devices including computers, mobile devices, tablets, servers and the like. For example, the interface unit 110 can include at least one of a serial port, a parallel port or a USB port that provides USB connectivity. The interface unit 110 can also include at least one of an Internet, a Local Area Network (LAN), an Ethernet, a Firewire, a modem or a digital subscriber line connection. In some embodiments, various combinations of these elements may be incorporated within the interface unit 110. The interface unit 110 can allow the electronic device 102 to send control signals to and receive data from the eye tracking device 134.

The communication unit 114 can be a radio that communicates utilizing CDMA, GSM, GPRS or Bluetooth protocol according to standards such as IEEE 802.11a, 802.11b, 802.11g, or 802.11n. The communication unit 114 can be used by the electronic device 102 to communicate with other devices or computers. The communication unit 114 can be a radio that communicates utilizing CDMA, GSM, GPRS or Bluetooth protocol according to standards such as IEEE 802.11a, 802.11b, 802.11g, or 802.11n. The communication unit 114 can provide the processing unit 104 with a way of communicating wirelessly with various devices that may be remote from the system 100. In some embodiments, the communication unit 114 may be optional.

The power supply unit 116 can be any suitable power source or power conversion hardware that provides power to the various components of the electronic device 102. The power supply unit 116 may be a power adaptor or a rechargeable battery pack depending on the implementation of the electronic device 102 as is known by those skilled in the art. In some cases, the power supply unit 116 may include a surge protector that is connected to a mains power line and a power converter that is connected to the surge protector (both not shown). The surge protector protects the power supply unit 116 from any voltage or current spikes in the main power line and the power converter converts the power to a lower level that is suitable for use by the various elements of the electronic device 102. In other embodiments, the power supply unit 116 may include other components for providing power or backup power as is known by those skilled in the art.

The memory unit 118 includes and non-volatile storage such as ROM, one or more hard drives, one or more flash drives or some other suitable data storage elements. The non-volatile storage may be used to store software instructions, including computer-executable instructions, for implementing the operating system 120, the programs 122 and other software modules, as well as storing any data used by these software modules. The data may be stored in the database(s) 132 and/or data files 130, such as for data relating to patients that are scheduled to undergo surgery. The data files 130 can be used to store data for the electronic device 102 such as, but not limited to, device settings, eye tracking device settings, calibration data, three-dimensional models of anatomical structures and quality metrics for trajectories. The files 132 can also store other data required for the operation of the surgical trajectory planning application 126 or the operating system 122 such as dynamically linked libraries and the like.

The I/O (input/output) module 124 includes software instructions that, when executed by the processor(s) of the processing unit 104, can configure the processor(s) to obtain a selection of a target site, obtain eye tracking data, obtain a selection of an optimal viewing angle, store data in the files 130 or database(s) 132 and/or retrieve data from the files 130 or database(s) 132. For example, the I/O module 124 may be used to receive eye tracking data obtained by the eye tracking device 124.

In another aspect, the I/O (input/output) module 124 includes software instructions that, when executed by the processor(s) of the processing unit 104, configure the processor(s) to store any input data from the user, such as control inputs, operational parameters and/or patient data that is received through one of the GUIs.

The surgical trajectory planning application 126 can include various software instructions that, when executed by at the processor(s) of the processing unit 104, allow the user to interact with the electronic device 102 to perform various functions, such as, but not limited to, (a) displaying 202 a three-dimensional model of an anatomical structure of a patient, or rendering a three-dimensional model (b) obtaining eye tracking data, (c) determining a surgical trajectory avoiding critical structures, (d) extrapolating a surgical entry point based on the surgical trajectory and the intersection of the surgical trajectory and an outer surface of the anatomical structure, (e) evaluating the quality of the surgical trajectory, (f) displaying metrics associated with the quality of the surgical trajectory and/or (g) sending images of the surgical trajectory to another electronic device.

The GUI engine 120 includes software instructions that, when executed by the processor(s) of the processing unit 104, configure the processor(s) to generate various GUIs that are then output on the display device 106, or another visual output device. The GUI engine 120 also includes software instructions for displaying the three-dimensional model of an anatomical structure, surgical trajectories and various metrics associated with the quality of a surgical trajectory.

The eye tracking device 134 is implemented in hardware including circuitry that may be used to collect eye tracking data associated with a point of gaze of a user and transmit the eye tracking data to the electronic device 102 where it may be used for determining a surgical trajectory and a surgical entry point. The electronic device 102 may additionally receive eye tracking data from the eye tracking device 134 and display the point of gaze on the three-dimensional model. The eye tracking device 134 may be configured to transmit raw eye tracking data to the electronic device 102 or processed eye tracking data, for example, eye tracking data that has been processed to reduce jitter.

The eye tracking device 134 includes sensor(s), such as, but not limited to, optical sensor(s) for tracking movement of the user's pupils and can include light source(s), such as, but not limited to near-infrared light source(s) for illuminating the user's pupils, in which cases the sensor(s) may be configured to detect light signals reflected from the user's pupils to determine the user's point of gaze. The eye tracking device 134 can include a communication that can include a USB interface, a Bluetooth radio, or a WiFi radio to transmit eye tracking data from the eye tracking device 134 to the electronic device.

In at least some embodiments, the eye tracking device 134 may be integrated into the electronic device 102, depending on the implementation of the electronic device 102. For example, in embodiments where the electronic device 102 is implemented using a VR head-mounted device, the eye tracking device 134 may be housed within the VR head-mounted device. In such embodiments, the eye tracking device 134 may share one or more components with the electronic device 102. For example, the power supply unit 116 of the electronic device 102 may supply power to the eye tracking device 134.

Figure 2:
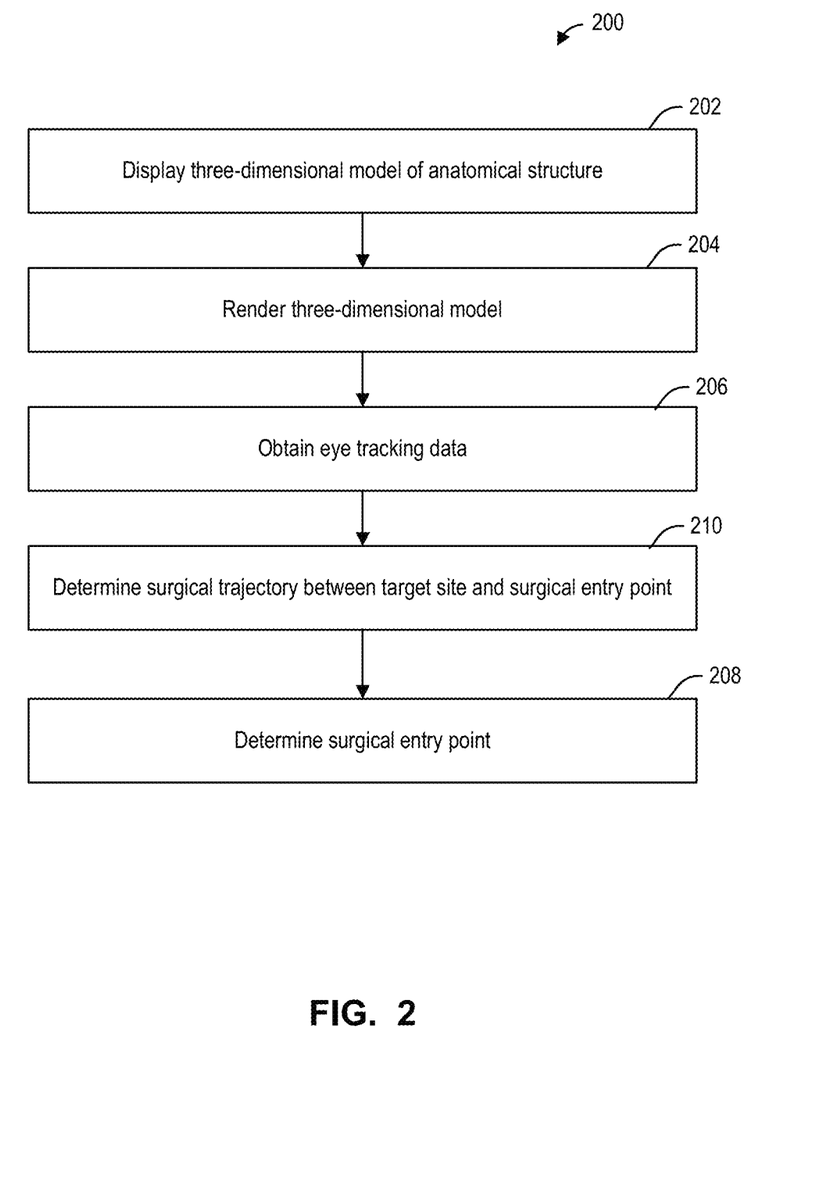
FIG. 2 shows a flowchart of an example embodiment of a method for surgical trajectory planning.

Referring now to FIG. 2, shown therein is a flowchart of an example embodiment of a method 200 for surgical trajectory planning. Method 200 can be performed by processor(s) of the processing unit 104 when executing software instructions of the various modules described earlier.

At 202, the method 200 involves displaying a three-dimensional model of the anatomical structure to be operated. The anatomical structure may be any anatomical structure that may require surgery, such as, but not limited to, an organ, or a portion of an organ. The three-dimensional model may show structures in the anatomical structure including, in some cases, vital anatomies, such as blood vessels and ventricles. The three-dimensional model may show the surface of the anatomical structure and the interior of the anatomical structure, for example, using see-through coloring. The three-dimensional model can be specific to the patient and may be obtained by imaging the anatomical structure of the patient requiring surgery using known imaging techniques. For example, the three-dimensional model may be obtained by obtaining magnetic resonance images (MRI) of the patient, though it will be appreciated that other medical imaging techniques may be used to obtain images of the anatomical structure of the patient. In some cases, three-dimensional modeling techniques can be applied to two-dimensional images or three-dimensional images of the anatomical structure of the patient to obtain a three-dimensional model of the anatomical structure. In other cases, the three-dimensional model may be constructed externally by a processor external to the system 100 and the processor(s) of the electronic device 102 may retrieve the three-dimensional model from a database.

In at least one embodiment, the three-dimensional model may be manipulable by the user. For example, the three-dimensional model may be rotated such that it may be viewed at various angles and magnified, such that portions of the three-dimensional model may be enlarged.

In some embodiments, the three-dimensional model of the anatomical structure may be displayed in a three-dimensional virtual reality environment. In such cases, the three-dimensional model may be described as a Voodoo doll model, where interactions acted on the three-dimensional model of the anatomical structure may be replicated onto the actual anatomical structure. In such cases, the method 200 can involve processing the two-dimensional or three-dimensional medical images of the patient to obtain a three-dimensional model viewable in a rendered 204 three-dimensional model of the actual anatomical structure, such as, for example, a virtual reality environment. Alternatively, the virtual reality three-dimensional model may be constructed by a processor external to the system 100 and the processor (s) may retrieve the virtual reality three-dimensional model of the anatomical structure. The virtual reality environment may be accessed via any virtual reality enabling device, including, but not limited to, a virtual reality head mounted device (HMD). In such cases, the method 200 can involve displaying the three-dimensional of the anatomical structure on the display(s) of the VR HMD. In at least one embodiment where the three-dimensional model of the anatomical structure is displayed in a virtual reality environment, the three-dimensional model of the anatomical structure may additionally be viewed at various angles by walking around the model.

The method 200 involves identifying a target site in the three-dimensional model. The target site can correspond to a surgical site and accordingly may be in the interior of the anatomical structure. For example, when the method 200 is used for surgical trajectory planning of brain surgery, the target site can correspond to an implantation site for a deep brain stimulation electrode. The location of the target site may be selected by the user. Alternatively, in some cases, the location of the target site may be determined by the processor(s) based on the type of surgery and/or may be predetermined given the type of surgery.

In at least one embodiment, determining a target site can involve inserting a visual marker at the target site in the three-dimensional model to identify the target site. In some cases, the three-dimensional model may be magnified prior to insertion of the visual marker, which may allow for increased accuracy when selecting the target site. When the system 100 is used for planning DBS surgery, the target sites may correspond to designated deep brain nucleus sites, such as the subthalamic nucleus (STN).

At 206, the method 200 involves determining a surgical trajectory between the target site and a surgical entry point. The surgical trajectory is obtained by capturing the optimal viewing angle based on a point of gaze of a user, determined based on eye tracking data. The optimal viewing angle may correspond to the angle of approach that may be used during the surgical procedure and may be dependent on the type of surgery. For example, for DBS, surgical entry points are preferably located in the frontal lobes. Accordingly, the optimal viewing angle for DBS may correspond to an angle that can allow for the surgical entry point to be in the frontal lobe. The optimal viewing angle may correspond to an angle that provides a clear line of sight of the target site to the user without obstructions or occlusions from substructures in the anatomical structure or without obstructions from vital anatomies, such as, but not limited to, blood vessels and ventricles within the anatomical structure.

For example, the user may search for a clear visual path while viewing the target site from the outside of the anatomical structure. The eye tracker 134 may collect eye tracking data relating to the point of gaze of the user while the user searches for the clear visual path.

In at least one embodiment, when the three-dimensional model is displayed in a virtual reality environment, the user may walk around the three-dimensional model to visually explore viable trajectories from various angles.

In some cases, the point of gaze of the user may be displayed on the three-dimensional model. For example, the point of gaze of the user may be displayed on the exterior surface of the anatomical structure, which can help in visualizing the surgical entry point, as described below. Alternatively or in addition thereto, the point of gaze of the user may be displayed in the interior of the anatomical structure which can help in for example, identifying if the line of sight is obstructed or occluded.

In at least one embodiment, prior to obtaining eye tracking data, the method 200 involves calibrating the eye tracker to the personal characteristics of the user.

At 208, the method 200 involves determining a surgical entry point on the surface of the anatomical structure. The surgical entry point may correspond to a point where an incision is to be made. The surgical entry point can correspond to the intersection of the point of gaze along the optimal viewing angle and the surface of the three-dimensional model, that is, the surgical entry point can correspond to the point on the surface of the anatomical structure viewed by the user.

In some cases, the surgical trajectory can be displayed such that it is viewable by the user. In some cases, the annotated three-dimensional model including the target site and the surgical trajectory may be saved in the database(s) such that it may be reviewed at a later time.

In at least some embodiments, the method 200 additionally involves evaluating the quality of the insertion trajectory. In some cases, evaluating the quality of the insertion trajectory can involve determining metrics associated with the insertion trajectory. For example, the depth of the trajectory may be calculated. Depending on the type of surgery, it may be desirable to minimize the depth of the trajectory to minimize risks.

In at least one embodiment, the method 200 can involve calculating the distance between point(s) in the anatomical structure and the nearest point on the insertion trajectory. The points can correspond to, for example, key structures in the anatomical structures or crucial anatomies, such as blood vessels or ventricles that are desirable to be avoided during surgery. In some cases, the surgical trajectory may be segmented into checking points and the distance between each checking point and the nearest key anatomical structure may be calculated.

In some cases, if the distance between point(s) in the anatomical structure is less than a predetermined threshold, the surgical trajectory may be identified as unsafe. For example, if one or more points in the anatomical structure are located within a predefined distance of the insertion trajectory, the insertion trajectory can be identified as an unsafe insertion trajectory and a notification may be displayed on or adjacent to the three-dimensional model. The predetermined distance may vary depending on the type of surgical procedure and the resolution of the three-dimensional model. For example, if a cannula used for a particular type of procedure has a typical diameter of 2 mm, the processor(s) may determine that a distance inferior to 2 mm between points in the anatomical structure and the surgical trajectory inferior is considered unsafe.

The metrics can be displayed on the three-dimensional model of the anatomical structure or adjacent to the anatomical structure.

Example 1: Simulation of Surgical Trajectory Planning Involving Untrained Participants A study was performed to assess the performance of a system for virtual-reality based deep brain stimulation trajectory planning. The study was performed using a commercially available head mounted display (HMD), the HTC Vive Pro Eye VR headset with Eye-tracking providing the virtual reality environment and its associated handheld controllers. The HMD used included eye tracking capabilities. Participants were asked to perform two tasks consecutively: target site selection and trajectory planning. Results obtained from the two tasks were analyzed.

Methods

Sample Size, Subjects, Setting 11 subjects (4 women, 7 men) between the ages of 25 and 35 were participated in the study. Participation was voluntary and informed consent was obtained. Most participants reported being familiar or somewhat familiar with VR technology and general brain anatomy. One participant reported having no knowledge of these two topics. All participants were right-handed. All participants were presented a presentation describing the clinical context, tasks, and goals of the study. The participants were also given a tutorial to familiarize themselves with the virtual reality environment and practice the designated tasks. The eye tracking device was also calibrated specifically to each participant at the start of the tutorial. During the tutorial, participants were shown numerical values of the trajectory depth and distances to important, key structures in the brain. A line showing the distance between the trajectory and the closest blood vessel or sulci was also displayed to assist the participants in visualizing the surgical risks. The participants were instructed to continue the tutorial until they felt comfortable using the system. On average, the participants spent 5.3±2.3 minutes in the tutorial environment.

Model Building

Figure 5:
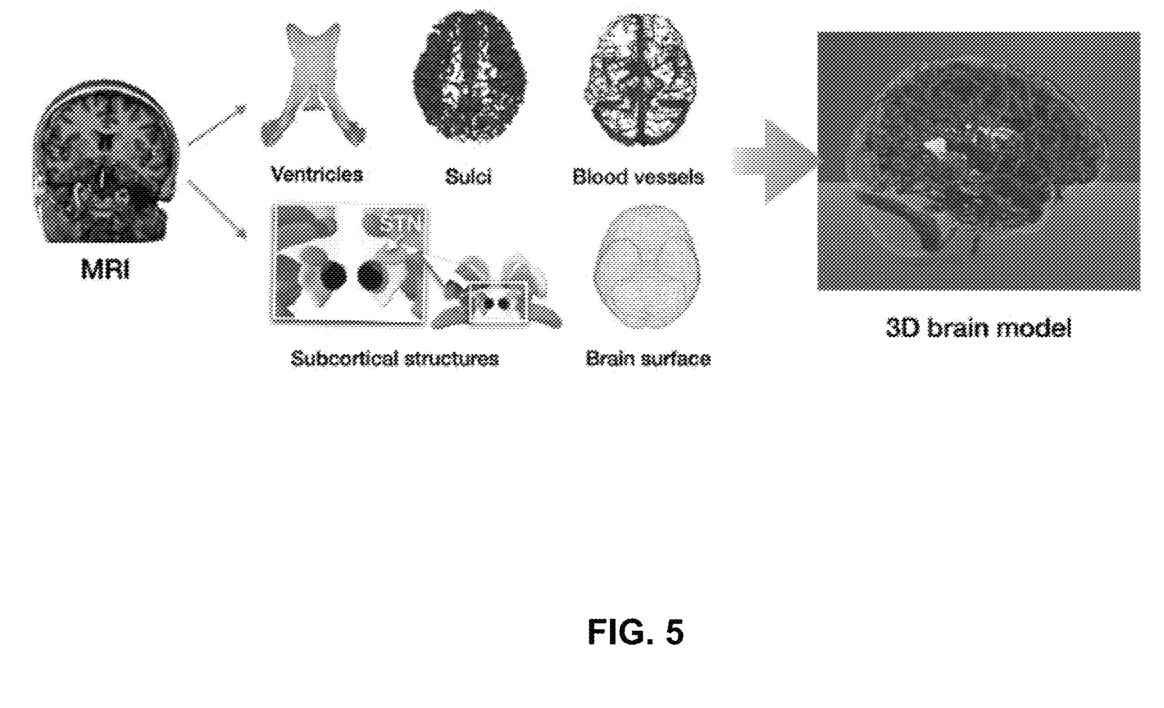
FIG. 5 shows substructures of a three-dimensional brain model used in the study.

A brain model viewable in a virtual reality environment was built using structural segmentations of MRI scans of a random subject from a publicly accessible database. Five sets of anatomical models were obtained: brain surface, cerebrovasculatures, subcortical nuclei, lateral ventricles and sulci, as shown in FIG. 5. In particular, a brain mask was extracted using a BEaST algorithm; blood vessels were segmented using the Frangi vesselness filter while constraining the operation within a dilated version of the brain mask to allow better delineation of the surface vessels. The vessel segmentation was then further manually revised by YX in ITKSNAP (http://itksnap.org). The subcortical nuclei were automatically identified by propagating high resolution nuclei labels from the MNI-PD25 atlas to the subject's anatomy using T2w-T2w nonlinear image registration. ANTs were used for the task. Lateral ventricles were segmented semi-automatically using the snake segmentation tool in ITKSNAP. Finally, sulci delineation was done by excluding ventricles from CSF segmentation results of T1w MRI using the FSL FAST algorithm while constraining the computation within the brain mask. As many smaller vessels often reside within the sulci and MRA may not fully capture these vessels, sulci are used as surrogates for finer blood vessels in DBS planning. All discrete anatomical labels were converted to polygon mesh models in .obj formats and used to construct the surgical scene.

Brain anatomical models were composited using distinct color coding to facilitate visual exploration. The ventricles, blood vessels, sulci and STN were colored in yellow, red, blue and green, respectively. The rest of the subcortical structures and the brain surface mesh were colored in various shades of grey and the brain surface model was rendered as a semi-transparent layer to allow visualization of the internal structures. The composition of the brain model was placed in a VR space in a "museum exhibition" mode with limited degrees of freedom for spatial manipulation, that is, the user was able to walk around the brain model to observe the brain model from various angles, rather than manipulate the model.

Figure 4:
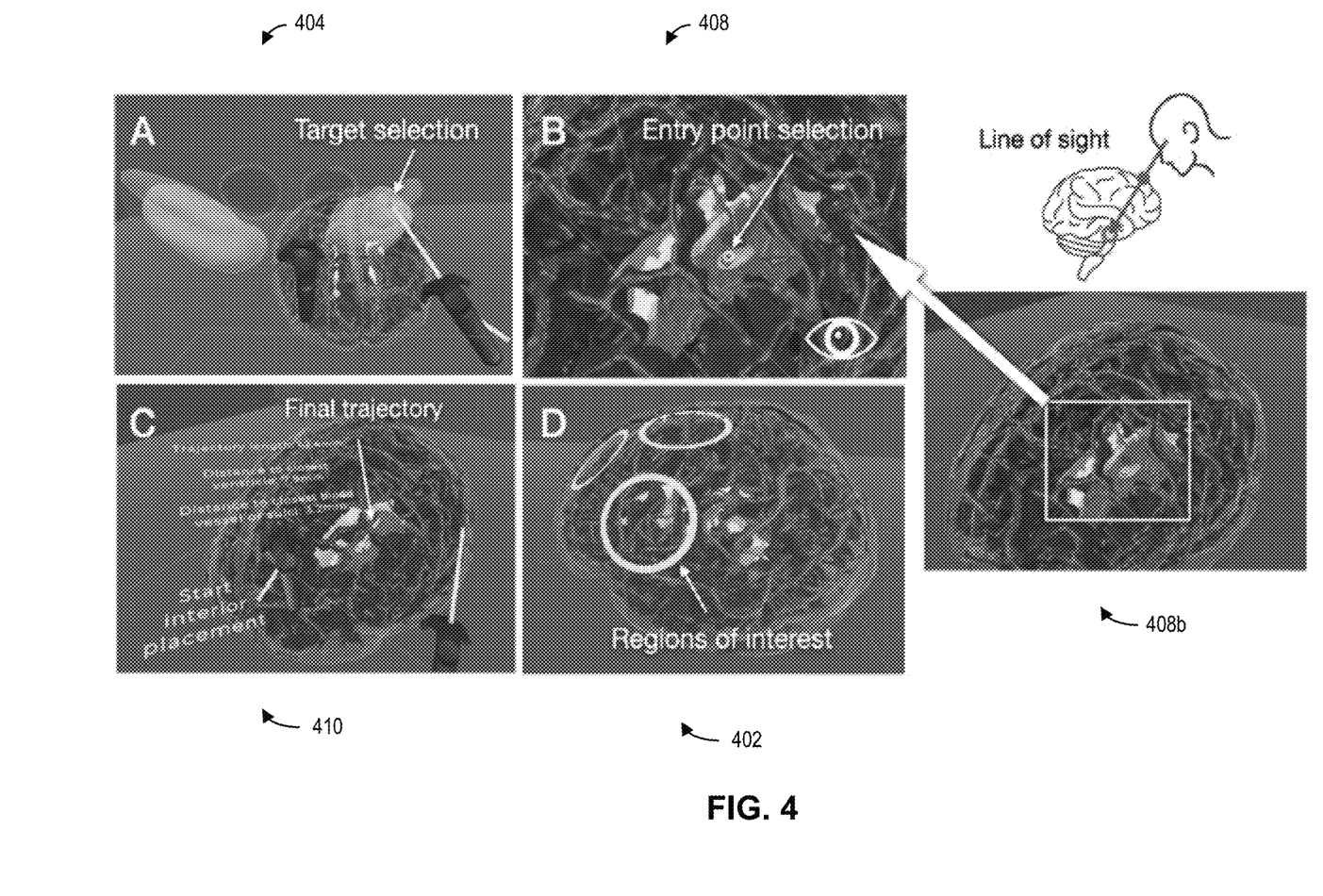
FIG. 4 shows images of the method for simulating surgical trajectory planning used in the study.

Given that the participants had limited medical expertise, three virtual rings were placed on the surface of each brain hemisphere to define regions of interest (ROI) and facilitate trajectory planning, as shown at 402 in FIG. 4.

Tasks

Figure 3:
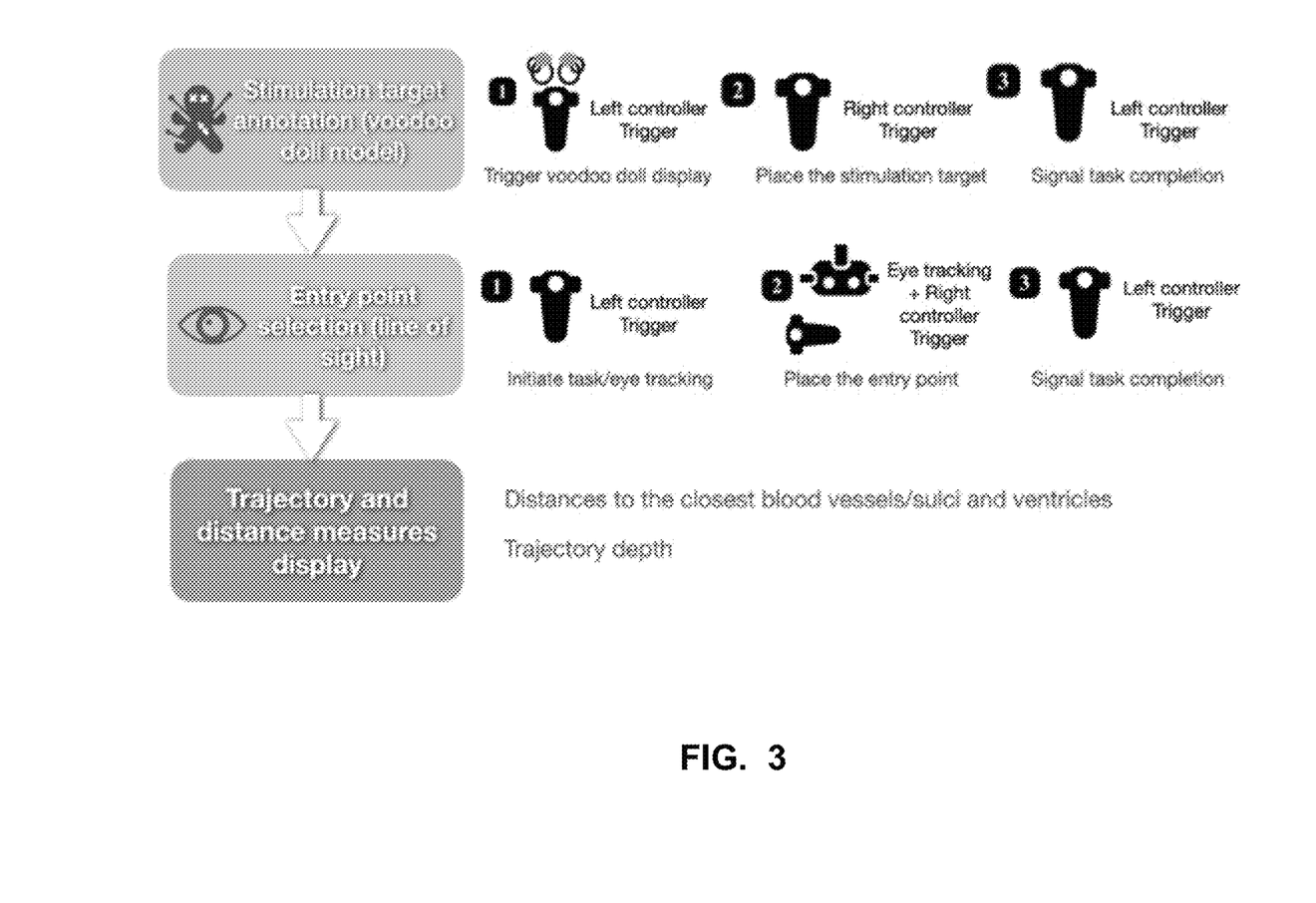
FIG. 3 shows a diagrammatic view of a method for simulating surgical trajectory planning used in a study.

As described, participants were tasked with two tasks: target site selection, also referred to as stimulation target annotation, and trajectory planning, or entry point selection. As shown in FIG. 3, to begin the tasks, participants were required to trigger the left controller. To place a stimulation target, the right controller was triggered, as shown at 404 in FIG. 4. To signal task completion, the left controller was triggered.

Once the first task was completed, the left controller was triggered again to signal task initiation and initiate the eye tracking capabilities of the VR HMD. Participants were then required to observe the three-dimensional model to determine a suitable entry point, as shown at 408 and 408b. Participants were instructed to find entry points suitable when the point provided a clear line of sight of the stimulation target placed during the first task. As shown in FIG. 4, to determine a suitable entry point, participants were required to look through the three-dimensional model to view the target site. Once a suitable entry point was found, the right controller was triggered to select the entry point. To signal completion, the left controller was triggered.

As shown at 410, metrics the trajectory was then shown to the user along with the trajectory length, the distance to the closest ventricle and the closest blood vessel or sulci were also displayed.

Participants were asked to place one electrode entry point in each of these ROIs to form a viable trajectory. In total, each participant was asked to place three trajectories in each hemisphere, that is, a total of six trajectories. The participants were asked to place three pairs of stimulation targets and entry points in the right hemisphere; the model was then rotated such that the left side was shown to the participant.

Results

Usability

To assess the usability of the system, the System Usability Scale (SUS) was used. The evaluation consisted of ten questions, each having a scale of 1 to 5. Participants were asked questions pertaining to the efficacy, and technical complexity of the system. Participants were also asked to provide their level of familiarity with VR technology and brain anatomy and general feedback questions.

Quantitative metrics were obtained from system used during completion of the two tasks. During the first task (i.e., stimulation target selection), the following metrics were recorded: distance (in mm) from the trajectory to the ventricles, smallest distance (mm) from the trajectory to the blood vessels/sulci, number of replacements before final point selection, time (in seconds) between starting and final point selection and insertion trajectory depth (in mm).

Nine participants expressed that the system was easy to use and/or the visualization was well executed. One participant particularly liked the voodoo doll interaction scheme.

Quantitative Evaluation of Trajectories

As discussed, distance and time metrics were collected. Table 1 below shows an overview of the results obtained. ROIs 1-3 were located on the right hemisphere and ROIs 4-6 were located on the left hemisphere. As the difficulty level in proposing a trajectory varied between different ROIs, the specific metrics from one ROI to another also differ. With the exception of ROI 5, the average time intervals to complete a trajectory were similar across all ROIs.

For task 1, for all six ROIs, the mean discrepancy between the selected stimulation target and the true COM was within 0.5 mm, for an MRI resolution of 1 mm. The average minimum distances from the trajectory to the vital structures were all above the predetermined safe threshold (2 mm).

The median value for the average number of replacements across all ROIs was 1.8 for task 1 and 0.3 for task 2.

The total time to propose a viable trajectory in Table 1 corresponds to the total time required to perform both task 1 and task 2. The mean total time was 59.6±41.4 seconds. The mean time for stimulation target selection (Task 1) was 23.0±22.7 seconds and the mean time for entry point selection (Task 2) was 36.7±20.9 seconds.

TABLE 1

| | Quantitative results for the proposed deep brain stimulation trajectories | | | | | |
|---|---|---|---|---|---|---|
| | ROI 1 | ROI 2 | ROI 3 | ROI 4 | ROI 5 | ROI 6 |
| Stimulation target distance (mm) | 0.2 ± 0.1 | 0.4 ± 0.2 | 0.3 ± 0.1 | 0.4 ± 0.1 | 0.4 ± 0.2 | 0.4 ± 0.1 |

TABLE 1-continued

Quantitative results for the proposed deep brain stimulation trajectories

|  | ROI 1 | ROI 2 | ROI 3 | ROI 4 | ROI 5 | ROI 6 |
|---|---|---|---|---|---|---|
| Minimum distance to ventricle (mm) | 8.3 ± 0.7 | 8.9 ± 0.3 | 5.0 ± 0.9 | 7.2 ± 1.7 | 8.2 ± 0.1 | 4.2 ± 0.4 |
| Minimum distance to blood vessels/sulci (mm) | 3.7 ± 0.8 | 2.1 ± 0.4 | 3.8 ± 0.6 | 3.1 ± 0.7 | 2.9 ± 0.4 | 3.1 ± 0.5 |
| Trajectory depth (mm) | 62.4 ± 0.3 | 60.0 ± 0.3 | 65.3 ± 0.6 | 63.6 ± 1.5 | 61.7 ± 0.6 | 64.5 ± 2.0 |
| Total time to propose a viable trajectory (s) | 60.3 ± 36.2 | 63.0 ± 32.7 | 60.9 ± 36.4 | 65.8 ± 63.0 | 42.8 ± 42.0 | 64.9 ± 71.3 |

Discussion of Results
Usability Evaluation

A mean±std SUS value of 86.4±10.4 with a range of 72.5-100 was obtained. A mean SUS over 68 is generally indicates a software system with above average usability. Using a two-tailed one-sample t-test, the collected SUSs were well above the threshold of 68 ($p<0.0002$).

The results obtained show that the employment of voodoo doll interaction with object magnification allows more precise point-based annotation within a small anatomical structure. Stimulation target placement was consistently within sub-millimeter accuracy, with standard deviations of only 0.1 or 0.2 mm. Taken together with the low number of replacements, these results indicate that the model performed excellently. The system's reliability was also demonstrated in the minimum distances to the key anatomical structures. Half of the trajectories had a distance of 8 mm or more from the ventricle and the blood vessels/sulci.

The time for devising a viable DBS was considerably short with our system. As discussed above, the mean planning time was 59.6 seconds among all participants, with the shortest mean time being 42.8 seconds for ROI 5. These assessments are notably shorter than previously reported values for DBS planning, both in 2D and in 3D. The results showed about an 80 second reduction in terms of DBS planning time when using 3D visualization and an even greater reduction when compared to conventional 2D DBS placement with multi-contrast MRI data, which was estimated to be about 40 minutes. These results confirm the high efficiency of the proposed system, in comparison to existing surgical planning platforms. The use of eye tracking technology also reduces muscle fatigue associated with using hand gestures to investigate viable surgical paths.

Limitations

In this study, a COM was used as a simplistic model to test the system and measure the perceptual accuracy. While the distances to the blood vessels, sulci, and lateral ventricles and the electrode insertion depth were considered, additional constraints, such as the distance to certain neural pathways, including the internal capsule, were not included in the model.

This study also involved a single subject model without reference trajectories defined by a surgeon. Thus, as described, participants were requested to perform trajectory planning in six designated local regions. In practice however, a viable DBS trajectory is not necessarily unique. Although defining multiple specific ROIs in the study can improve data diversity, this approach can also limit the range of quantitative assessments for quality trajectories.

Numerous specific details are set forth herein in order to provide a thorough understanding of the exemplary embodiments described herein. However, it will be understood by those of ordinary skill in the art that these embodiments may be practiced without these specific details. In other instances, well-known methods, procedures and components have not been described in detail so as not to obscure the description of the embodiments. Furthermore, this description is not to be considered as limiting the scope of these embodiments in any way, but rather as merely describing the implementation of these various embodiments.

We claim:

1. A method for surgical trajectory planning, the method comprising:
   rendering a three-dimensional model of an anatomical structure, said model including a target site within said anatomical structure;
   obtaining eye tracking data of a user relating to a point of gaze of said user as said user is gazing into said model and towards said target site;
   identifying a line of sight for the target site based on said point of gaze of said user, said line of sight corresponding to an optimal viewing angle for unobstructedly viewing the target site;
   determining a surgical trajectory along said line of sight between the target site and a surgical entry point on a surface of the anatomical structure based on the optimal viewing angle, the surgical entry point corresponding to an intersection of the line of sight and said surface of the three-dimensional model.

2. The method of claim 1, wherein displaying the three-dimensional model of the anatomical structure comprises displaying the three-dimensional model in a virtual reality or mixed reality environment.

3. The method of claim 1, wherein the eye tracking data is obtained from an eye tracker housed in a virtual reality head-mounted device.

4. The method of claim 1, wherein selecting a target site comprises inserting a visual marker at the target site in the three-dimensional model.

5. The method of claim 1, wherein the surgical trajectory is a straight line trajectory.

6. The method of claim 1, wherein the anatomical structure is a brain of a subject and the target site corresponds to an implantation site for a deep brain stimulation electrode.

7. The method of claim 1, further comprising evaluating a quality of the entry trajectory.

8. The method of claim 7, wherein determining the quality of the trajectory comprises calculating a distance between at least one point in the anatomical structure and a corresponding nearest point on the surgical trajectory.

9. The method of claim 8, further comprising:
when the distance between at least one of the at least one point is smaller than a predetermined threshold, identifying the trajectory as an unsafe trajectory.

10. The method of claim 7, further comprising:
displaying a metric associated with the quality of the surgical trajectory.

11. The method of claim 7, wherein determining the quality of the trajectory comprises calculating a depth of the surgical trajectory.

12. The method of claim 1, further comprising: displaying the surgical trajectory on the three-dimensional model.

13. The method of claim 1, wherein the three-dimensional model is obtained based on anatomical images of the anatomical structure of a subject.

14. A system for surgical trajectory planning in a three-dimensional model of an anatomical structure, said model including a target site within said anatomical structure, the system comprising:
an electronic device comprising at least one processor configured to:
obtain eye tracking data of a user relating to a point of gaze of said user as said user gazes into said model towards said target site;
identify a line of sight for the target site based on said point of gaze of said user, said line of sight corresponding to an optimal viewing angle for unobstructedly viewing the target site;
determine a surgical trajectory along said line of sight between the target site and a surgical entry point on a surface of the anatomical structure based on the optimal viewing angle, the surgical entry point corresponding to an intersection of the line of sight and said surface of the three-dimensional model;
wherein said surgical trajectory traces a path to said target site while avoiding key structures.

15. The system of claim 14, further comprising a virtual reality head-mounted device in communication with the at least one processor, and wherein the at least one processor is configured to display the three-dimensional model of the anatomical structure in a virtual reality environment using the virtual reality head-mounted device.

16. The system of claim 15, wherein the virtual reality head-mounted device houses the eye tracker.

17. The system of claim 14, wherein the at least one processor is configured to insert a visual marker at the target site in the three-dimensional model.

18. The system of claim 14, wherein the entry trajectory is a straight line trajectory.

19. The system of claim 14, wherein the anatomical structure is a brain of a subject and the target site corresponds to an implantation site for a deep brain stimulation electrode.

20. The system of claim 14, wherein the at least one processor is further configured to evaluate a quality of the surgical trajectory.

21. The system of claim 20, wherein the at least one processor is further configured to calculate a distance between at least one point in the anatomical structure and a corresponding nearest point on the surgical trajectory.

22. The method of claim 21, wherein the at least one processor is further configured to: when the distance between at least one of the at least one point is smaller than a predetermined threshold, identify the trajectory as an unsafe trajectory.

23. The method of claim 20, wherein the at least one processor is further configured to:
display a metric associated with the quality of the surgical trajectory.

24. The system of claim 20, wherein the at least one processor is further configured to calculate a depth of the surgical trajectory.

25. The system of claim 14, wherein the at least one processor is configured to:
display the surgical trajectory on the three-dimensional model.

26. The system of claim 14, wherein the three-dimensional model is obtained based on anatomical images of the anatomical structure of a subject.

* * * * *